(12) United States Patent
Tsai et al.

(10) Patent No.: US 9,587,284 B2
(45) Date of Patent: Mar. 7, 2017

(54) LACTIC ACID BACTERIUM HAVING IMMUNOMODULATORY AND ANTI-ALLERGIC EFFECTS AND PHARMACEUTICAL COMPOSITION CONTAINING THE SAME

(71) Applicant: Asian Probiotics and Prebiotics Ltd., Victoria Mahe (SC)

(72) Inventors: Ying-Chieh Tsai, Taipei (TW); Tan-Wei Liao, Taipei (TW); Yen-Wenn Liu, Taipei (TW); Yu-Han Chen, Taipei (TW); Chien-Chen Wu, Taipei (TW)

(73) Assignee: Asian Probiotics and Prebiotics Ltd., Victoria, Mahe (SC)

( * ) Notice: Subject to any disclaimer, the term of this patent is extended or adjusted under 35 U.S.C. 154(b) by 24 days.

(21) Appl. No.: 14/186,069

(22) Filed: Feb. 21, 2014

(65) Prior Publication Data

US 2015/0240200 A1    Aug. 27, 2015

(51) Int. Cl.

| | |
|---|---|
| *C12N 1/00* | (2006.01) |
| *C12R 1/25* | (2006.01) |
| *A61K 35/747* | (2015.01) |
| *A61K 39/36* | (2006.01) |
| *A61K 39/00* | (2006.01) |

(52) U.S. Cl.
CPC ................ *C12R 1/25* (2013.01); *A61K 39/36* (2013.01); *A61K 2039/521* (2013.01); *A61K 2039/58* (2013.01)

(58) Field of Classification Search
None
See application file for complete search history.

(56) References Cited

PUBLICATIONS

Liu et al. 2014 (Oral Administration of Heat-Inactivated Lactobacillus plantarum K37 Modulated Airway Hyperresponsiveness in Ovalbumin-Sensited BALB/c Mice; PLOS ONE 9(6): 1-11).*
Chao et al. 2009 (Diversity of lactic acid bacteria in suan-tsai and fu-tsai, traditional fermented mustard products of Taiwan; International Journal of Food Microbiology 135: 203-210).*
Wesche et al. 2009 (Stress, Sublethal Injury, Resuscitation, and Virulence of Bacterial Foodborne Pathogens; J Food Prot 72(5):1121-1138).*
Williams et al. 2012 (F1000 Medical Reports; vol. 4(24): 1-5).*
Zosky et al. 2007 (Ovalbumin-sensitized mice are good models for airway hyperresponsiveness but not acute physiological responses to allergen inhalation; Experimental Models in Allergic Disease; Clinical and Experimental Allergy 38:829-838; see abstract).*

* cited by examiner

*Primary Examiner* — Gary Nickol
*Assistant Examiner* — Mary Lyons
(74) *Attorney, Agent, or Firm* — McCarter & English, LLP; Yu Lu

(57) ABSTRACT

The present invention provides an isolated lactic acid bacterium, *Lactobacillus plantarum* subsp. *plantarum* K37 strain, deposited in DSME-DEUTSCHE SAMMLUNG VON MIKROORGANISMEN UND ZELLKULTUREN GmbH under Accession No. DSM 27445. The present invention further provides a pharmaceutical composition comprising the isolated lactic acid bacterium (*Lactobacillus plantarum* subsp. *plantarum* K37). Moreover, the present invention provides a method for preventing or treating a disorder in a subject, comprising a step of administering an effective amount of the isolated lactic acid bacterium (*Lactobacillus plantarum* subsp. *plantarum* K37) to the subject.

13 Claims, 9 Drawing Sheets

SEQUENCE LISTING

<160> NUMBER OF SEQ ID NOS: 6

<210> SEQ ID NO 1
<211> LENGTH: 1111
<212> TYPE: DNA
<213> ORGANISM: Lactobacillus plantarum subsp. plantarum K37
<220> FEATURE:
<221> NAME/KEY: gene
<223> OTHER INFORMATION: partial sequence of 16S rDNA

<400> SEQUENCE: 1

| ggaacctaat | acatgcaagt | cgaacgaact | ctggtattga | ttggtgcttg | catcatgatt | 60 |
| tacatttgag | tgagtggcga | actggtgagt | aacacgtggg | aaacctgccc | agaagcgggg | 120 |
| gataacacct | ggaaacagat | gctaataccg | cataacaact | tggaccgcat | ggtccgagtt | 180 |
| tgaaagatgg | cttcggctat | cacttttgga | tggtcccgcg | gcgtattagc | tagatggtgg | 240 |
| ggtaacggct | caccatggca | atgatacgta | gccgacctga | gagggtaatc | ggccacattg | 300 |
| ggactgaaac | acggcccaaa | ctcctacggg | aggcagcagt | agggaatctt | ccacaatgga | 360 |
| cgaaagtctg | atggagcaac | gccgcgtgag | tgaagaaggg | tttcggctcg | taaaactctg | 420 |
| ttgttaaaga | agaacatatc | tgagagtaac | tgttcaggta | ttgacggtat | ttaaccagaa | 480 |
| agccacggct | aactacgtgc | cagcagccgc | ggtaatacgt | aggtggcaag | cgttgtccgg | 540 |
| atttattggg | cgtaaagcga | gcgcaggcgg | ttttttaagt | ctgatgtgaa | agccttcggc | 600 |
| tcaaccgaag | aagtgcatcg | gaaactggga | aacttgagtg | cagaagagga | cagtggaact | 660 |
| ccatgtgtag | cggtgaaatg | cgtagatata | tggaagaaca | ccagtggcga | aggcggctgt | 720 |
| ctggtctgta | actgacgctg | aggctcgaaa | gtatgggtag | caaacaggat | tagataccct | 780 |
| ggtagtccat | accgtaaacg | atgaatgcta | agtgttggag | ggtttccgcc | cttcatgctg | 840 |
| cagctaacgc | attagcattc | cgctggggag | tacggtcgca | gctgaactca | gagtattgac | 900 |
| gaggtccgca | cagcgtgcag | catgtgttta | attcgagcta | cgcgaagatc | gtacagctga | 960 |
| catactatgc | agtctagaaa | taacgtcctt | cgggaactga | tacagtggtg | cagtgtctca | 1020 |
| gctcggtcct | ggatgtgggt | tagtccgacg | aggcacctta | tatcagtgca | gctacttgtc | 1080 |
| tctggtgaac | tgacgtgaca | acgcagcagt | g | | | 1111 |

<210> SEQ ID NO 2
<211> LENGTH: 474
<212> TYPE: DNA
<213> ORGANISM: Lactobacillus plantarum subsp. plantarum K37
<220> FEATURE:
<221> NAME/KEY: gene
<223> OTHER INFORMATION: partial sequence of phes

<400> SEQUENCE: 2

| gggattctat | tacaagacgt | gctactacgc | acgcagacgt | ctgctgatca | gccgcggtca | 60 |
| cttgaaaatc | acgatttttc | taaaggaccg | ctgaaggtct | tgtcacctgg | ccgcgtttat | 120 |
| cggcgtgata | cggatgatgc | aacccattcc | catcaatttc | atcaaattga | agggttagtc | 180 |
| gtggacaagc | atattacgat | ggctgatttg | aagggcacct | taattctggt | tgccaagact | 240 |
| ttgtttggcg | atcaattcga | tgttcggcta | cggccaagct | tctttccatt | cacggaacca | 300 |
| tccgtagaag | ctgatgtaac | ttgctttaat | tgcaatggca | agggctgtgc | aatctgtaag | 360 |
| caaacgggtt | ggatcgaagt | actgggtgcc | ggcatggttc | accccacgt | gttagaaatg | 420 |
| tctggcattg | atccagaaga | atatggtggc | tttgctttcg | gggcctttgg | aaca | 474 |

```
<210> SEQ ID NO 3
<211> LENGTH: 22
<212> TYPE: DNA
<213> ORGANISM: artificial
<220> FEATURE:
<223> OTHER INFORMATION: An artificially synthesized nucleotide sequence

<400> SEQUENCE: 3
atgtaagctc tgggggattc ac                                              22

<210> SEQ ID NO 4
<211> LENGTH: 22
<212> TYPE: DNA
<213> ORGANISM: artificial
<220> FEATURE:
<223> OTHER INFORMATION: An artificially synthesized nucleotide sequence

<400> SEQUENCE: 4
aagtaagtga ctggggtgag cg                                              22

<210> SEQ ID NO 5
<211> LENGTH: 10
<212> TYPE: DNA
<213> ORGANISM: artificial
<220> FEATURE:
<223> OTHER INFORMATION: An artificially synthesized nucleotide sequence

<400> SEQUENCE: 5
gcggaaatag                                                            10

<210> SEQ ID NO 6
<211> LENGTH: 10
<212> TYPE: DNA
<213> ORGANISM: artificial
<220> FEATURE:
<223> OTHER INFORMATION: An artificially synthesized nucleotide sequence

<400> SEQUENCE: 6
ctcaggtcgc                                                            10
```

LACTIC ACID BACTERIUM HAVING IMMUNOMODULATORY AND ANTI-ALLERGIC EFFECTS AND PHARMACEUTICAL COMPOSITION CONTAINING THE SAME

BACKGROUND OF THE INVENTION

1. Field of the Invention

This invention relates to a lactic acid bacterium, and more particularly relates to a novel lactic acid bacterium strain having immunomodulatory and anti-allergic effects in a subject.

2. Description of Related Art

Allergic disorders, such as allergic rhinitis, atopic dermatitis, allergic asthma and food allergies, have become increasingly prevalent in many countries. These disorders not only affect the individual's life quality but also become a medical burden on society. Allergies are related to the T-helper cell type 2 (Th2) responses in both T-cells and B-cells. Th2 responses are characterized by the production of certain cytokines including interleukin (IL)-4, -5, -13, and the production of total immunoglobulin (Ig) E, antigen-specific IgE and IgG1. Th2 cytokines produced by Th2 cells enhance IgE production and eosinophil accumulation. Among the Th2 cytokines, IL-5 is known to be important to the differentiation, maturation and recruitment of eosinophils while both IL-4 and IL-13 are promising targets for therapeutic intervention in asthma and other Th2-associated diseases. Furthermore, IL-13 directly enhances mucus hypersecretion and airway hyperresponsiveness (AHR). Cytokine production is regarded as T-cell response while immunoglobulin production is regarded as B-cell response. Th1 cells can suppress Th2 responses by secreting interferon (IFN)-γ, IgG2a, IL-2, and IL-3. Therefore, to regulate the immune responses by suppressing Th2-responses while enhancing Th1-responses is expected to be helpful in the treatment of allergy and other Th2-dominant disorders, such as asthma which is a chronic, complex respiratory disease caused by various airway obstructions, airway eosinophil inflammation and bronchial hyperresponsiveness.

Numerous studies have proposed that lactic acid bacteria (LAB), either live or heat-killed, alleviate allergic symptoms by modulating Th1/Th2 responses toward a Th1-dominant state. For example, live *Lactobacillus paracasei* KW3110 was orally administered to allergic mice and the results revealed anti-allergic effects on both Th1 and Th2 cytokines including IL-12 induction and IL-4 repression. Heat-killed *Lactobacillus casei* strain Shirota (LcS) stimulated IL-12 secretion, which shifted the cytokine production pattern from a Th2 to a Th1 predominance and thereby suppressed IgE production, IgG1 responses and systemic anaphylaxis in human. Heat-killed *Lactobacillus brevis* SBC8803 inhibited IgE production and histamine secretion due to the improvement of the Th1/Th2 balance toward Th1 dominance. Heat-treated *Lactobacillus acidophilus* strain L-55 was orally administered to ovalbumin (OVA)-sensitized BALB/c mice and the results showed inhibiting the nasal symptoms, sneezing and nasal rubbing induced by OVA challenge. Thus, either live or heat-killed LAB exhibits the capacity to ameliorate allergic responses in murine or in human.

In the present invention, *Lactobacillus plantarum* subsp. *plantarum* K37 (hereinafter referred to K37), isolated from fu-tsai, traditional fermented mustard products of Taiwan, is selected because of its profound immunomodulatory potency in vitro by inducing higher levels of IFN-γ production in human peripheral blood mononuclear cells (hPB-MCs). Different amounts of K37, such as $10^5$, $10^7$, and $10^9$ CFU (colony forming unit), are orally administered to OVA-sensitized and OVA-challenged BALB/c mice. The effects of K37 on systemic allergy are investigated by determining serum levels of Igs and cytokines. The AHR against methacholine is evaluated using non-invasive whole body plethysmography. The histological analysis is also assessed.

SUMMARY OF THE INVENTION

The present invention provides an isolated lactic acid bacterium for immunomodulation, *Lactobacillus plantarum* subsp. *plantarum* K37 strain, deposited in DSME-DEUTSCHE SAMMLUNG VON MIKROORGANISMEN UND ZELLKULTUREN GmbH under Accession No. DSM 27445.

The present invention further provides a pharmaceutical composition for preventing or treating a disorder in a subject comprising the lactic acid bacterium for immunomodulation, *Lactobacillus plantarum* subsp. *plantarum* K37, and an excipient.

In one embodiment of the present invention, the lactic acid bacterium is a heat-inactivated bacterium. The lactic acid bacterium is orally administered to a subject.

In one embodiment of the present invention, the pharmaceutical composition is for preventing or treating a disorder in a subject. In one embodiment of the present invention, a cell number in the subject is decreased and wherein the cell is selected from the group consisting of macrophage, eosinophil, neutrophil and lymphocyte.

In one embodiment of the present invention, the disorder is related to an allergic disorder. In one embodiment of the present invention, the allergic disorder is selected from the group consisting of allergic rhinitis, atopic dermatitis, allergic asthma, food allergies and airway hyperresponsiveness.

In one embodiment of the present invention, the allergic disorder is related to an expression of a protein selected from the group consisting of IgG1, IgG2a, IgE, IFN-γ, TNF-α, IL-2, IL-4, IL-5, IL-6, IL-12, IL-13 and eotaxin. In one embodiment of the present invention, the expression of IL-2, IL-12 and IFN-γ is increased. In one embodiment of the present invention, the expression of IL-4, IL-5, IL-13, TNF-α, eotaxin and IgE is decreased.

The present invention further provides a method for preventing or treating a disorder in a subject, comprising a step of administering an effective amount of the lactic acid bacterium for immunomodulation, *Lactobacillus plantarum* subsp. *plantarum* K37, to the subject.

BRIEF DESCRIPTION OF THE DRAWINGS

FIG. 5A shows total counts of cells in bronchoalveolar lavage fluid (BALF) from the healthy control group (CON), the allergy control group (OVA), K37-L ($10^5$ CFU, heat-killed), K37-M ($10^7$ CFU, heat-killed), K37-H ($10^9$ CFU, heat-killed), and K37-A ($10^9$ CFU, live) groups of mice. FIG. 5B shows cell fractions of macrophage, eosinophil, neutrophil and lymphocyte in BALF were analyzed and are expressed as means±SD of six mice in each group. A difference between K37 groups and OVA group was considered statistically significant when $P<0.05$ (*) and $P<0.01$ (**).

DETAILED DESCRIPTION OF THE PREFERRED EMBODIMENTS

Figure 1:
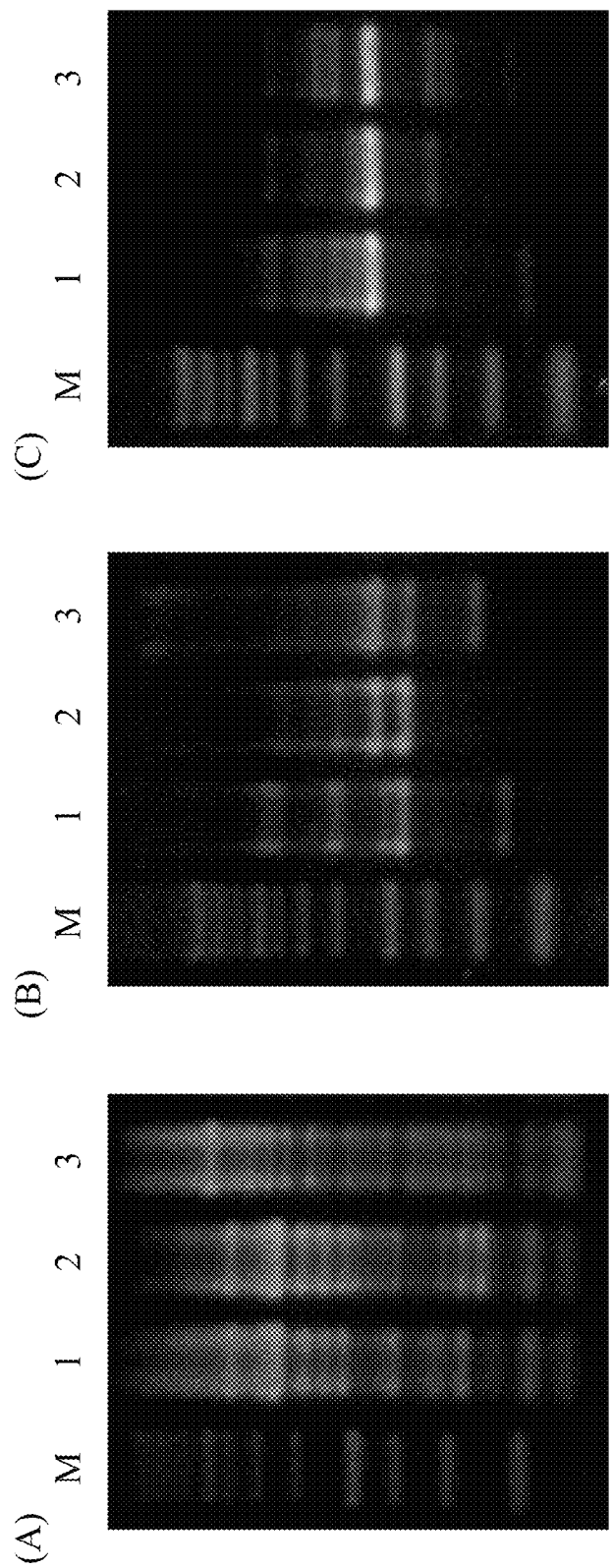
FIG. 1A to FIG. 1C are electrophoresis photographs showing the PCR-fingerprinting profiles of *Lactobacillus plantarum* strains, in which primers represented by SEQ ID NO: 3/NO: 4 (FIG. 1A), NO: 5 (FIG. 1B) and NO: 6 (FIG. 1C) were used. Lane M, DNA ladder (250-10000 bp); Lane 1, *Lactobacillus plantarum* subsp. *plantarum* K37; Lane 2, *Lactobacillus plantarum* subsp. *plantarum* ATCC 14917$^T$; Lane 3, *Lactobacillus plantarum* subsp. *argentoratensis* ATCC 17638$^T$.

The following specific examples are used for illustrating the present invention. A person skilled in the art can easily conceive the other advantages and effects of the present invention. The present invention can also be implemented by different specific cases be enacted or application, the details of the instructions can also be based on different perspectives and applications in various modifications and changes do not depart from the spirit of the creation.

Many examples have been used to illustrate the present invention. The examples sited below should not be taken as a limit to the scope of the invention.

EXAMPLES

Example 1

Isolation and Genetic Typing of *Lactobacillus plantarum* Subsp. *plantarum* K37

*Lactobacillus plantarum* subsp. *plantarum* K37 (hereinafter referred to K37) was isolated from fu-tsai, traditional fermented mustard products of Taiwan. To identify species of K37, a combined use of 16S rDNA and pheS sequences was performed. 16S rDNA (SEQ ID NO: 1) and pheS (SEQ ID NO: 2) from K37 were analyzed by direct sequencing of about 500 nucleotides of PCR-amplified product. Genomic DNA extraction, PCR mediated amplification, purification of the PCR products, and sequencing of the purified PCR products were carried out, accordingly.

The resulting sequence was put into the alignment software provided online by the National Center for Biotechnology Information (NCBI) (http://www.ncbi.nlm.nih.gov/), aligned manually and compared with representative 16S rDNA or pheS sequences of organisms belonging to the *Lactobacillus*, respectively. For comparison, 16S rDNA and pheS sequences were also obtained from the database provided online by the NCBI.

As a result of this analysis, the following Table 1 lists those organisms, whose 16S rDNA (Table 1A) and pheS (Table 1B) sequences show the highest similarity values compared to the sequence of K37.

TABLE 1

Comparison Between 16S rDNA (A) and pheS (B) Sequences (A)

| | % 16S rDNA sequence similarity to K37 |
|---|---|
| *Lactobacillus pentosus* (D79211) | 99.8 |
| *Lactobacillus plantarum* subsp. *plantarum* (D79210) | 99.6 |
| *Lactobacillus paraplantarum* (AJ306297) | 99.5 |
| *Lactobacillus plantarum* subsp. *argentoratensis* (AJ640078) | 98.8 |

TABLE 1-continued

Comparison Between 16S rDNA (A) and pheS (B) Sequences

| Lactobacillus collinoides (AB005893) | 92.4 |
| Lactobacillus brevis (M58810) | 92.2 |
| Lactobacillus buchneri (AB205055) | 90.3 |
| Lactobacillus fermentum (M58819) | 88.9 |

(B)

| | % pheS gene sequence similarity to K37 |
|---|---|
| Lactobacillus plantarum subsp. plantarum (AM087714) | 99.5 |
| Lactobacillus plantarum subsp. argentoratensis (AM694185) | 90.9 |
| Lactobacillus paraplantarum (AM087727) | 90.0 |
| Lactobacillus collinoides (AM087730) | 66.8 |
| Lactobacillus brevis (AM087680) | 65.8 |
| Lactobacillus buchneri (AM087681) | 65.8 |
| Lactobacillus fermentum (AM087693) | 63.5 |
| Lactobacillus pentosus (AM087713) | 58.1 |

The combined result of sequence analysis of 16S rDNA and pheS of K37 shows highest similarity to *Lactobacillus plantarum* subsp. *plantarum*. Consequently, K37 represents a strain of *Lactobacillus plantarum* subsp. *plantarum*.

*Lactobacillus plantarum* subsp. *plantarum* K37 has been deposited under Budapest Treaty at DSMZ-DEUTSCHE SAMMLUNG VON MIKROORGANISMEN UND ZELLKULTUREN GmbH (Inhoffenstr. 7 B, D-38124 Braunschweig, Germany) on Jun. 27, 2013 and has been given the DSMZ Accession No. DSM 27445 by the International Depositary Authority. This biological material was subjected to the viability test and passed.

Example 2

Identification of the Bacterial Strains Using PCR-Fingerprinting

The PCR-fingerprinting profiles of K37 and the other two *Lactobacillus plantarum* type strains were compared. PCR was carried out under the condition indicated in Table 2. DNAs extracted from these strains were used as templates. The obtained amplification products were electrophoresed and the patterns were compared as shown in FIG. 1A to FIG. 1C, in which primers represented by SEQ ID NO: 3/NO: 4 (FIG. 1A), NO: 5 (FIG. 1B) and NO: 6 (FIG. 1C) were used.

TABLE 2

Composition of the PCR reaction solution (25 μl)

| Component | Volume |
|---|---|
| ddH$_2$O | 17.9 μl |
| 10X PCR Buffer | 2.5 μl |
| dNTP Mix (2.5 mM) | 2.0 μl |
| MgCl$_2$ (25 mM) | 1.0 μl |
| primer | 0.4 μl |
| rTaq | 0.2 μl |
| DNA template (10 μM) | 1.0 μl |

PCR Conditions:
94° C., 2 min.; 5 cycles (94° C., 30 sec.; 36° C., 1 min.; 72° C., 1.5 min.); 30 cycles (94° C., 20 sec.; 36° C., 30 sec.; 72° C., 1.5 min.); 72° C., 3 min.

As shown in FIG. 1A to FIG. 1C, Lane M represents DNA ladder (250-10000 bp); Lane 1 represents *Lactobacillus plantarum* subsp. *plantarum* K37; Lane 2 represents *Lactobacillus plantarum* subsp. *plantarum* ATCC 14917$^T$; Lane 3 represents *Lactobacillus plantarum* subsp. *argentoratensis* ATCC 17638$^T$. The results indicated that the amplified products of K37 had different patterns from other two *Lactobacillus plantarum* strains.

Example 3

Analytical Profile Index (API) Typing

Sugar utilization for K37 used in the present invention was investigated using API50CHL kit (bioMerieux, France), and the results are shown in Table 3. The fermentation test indicates that K37 harbor a biochemical property similar to *Lactobacillus plantarum* subsp. *plantarum*.

TABLE 3

Results of Fermentation Test[a]

| carbohydrates substrate | K37 (DSM 27445) |
|---|---|
| CONTROL | − |
| Glycerol | − |
| Erythritol | − |
| D-Arabinose | − |
| L-Arabinose | + |
| D-Ribose | + |
| D-Xylose | − |
| L-Xylose | − |
| D-Adonitol | − |
| Methyl-β-D-Xylopyranoside | − |
| D-Galactose | + |
| D-Glucose | + |
| D-Fructose | + |
| D-Mannose | + |
| L-Sorbose | − |
| L-Rhamnose | + |
| Dulcitol | − |
| Inositol | − |
| D-Mannitol | + |
| D-Sorbitol | + |
| Methyl-α-D-mannopyranoside | + |
| Methyl-α-D-glucopyranoside | − |
| N-Acetyl glucosamine | + |
| Amygdalin | + |
| Arbutin | + |
| Esculin ferric citrate | + |
| Salicin | + |
| D-Cellobiose | + |
| D-Maltose | + |
| D-Lactose (bovine origin) | + |
| D-Melibiose | + |
| D-Saccharose (sucrose) | + |
| D-Trehalose | + |
| Inulin | + |
| D-Melezitose | + |
| D-Raffinose | + |
| Amidon (starch) | − |
| Glycogen | − |
| Xylitol | − |
| Gentiobiose | + |
| D-Turanose | + |
| D-Lyxose | − |
| D-Tagatose | − |
| D-Fucose | − |
| L-Fucose | − |
| D-Arabitol | − |
| L-Arabitol | − |
| Potassium gluconate | + |
| Potassium 2-ketogluconate | − |
| Potassium 5-ketogluconate | − |

[a]+, positive; −, negative

Example 4

In Vivo Evaluation of Anti-Allergic Action of K37

1. Materials and Methods (1) Chemicals and Reagents de Man, Rogosa, and Sharpe (MRS) broth was purchased from Difco (Sparks, Md.). Methacholine and OVA were purchased from Sigma-Aldrich (St. Louise, Mo.). RPMI-1640 culture medium, fetal bovine serum (FBS), L-glutamate, antibiotics (penicillin, streptomycin, and amphotericin) were obtained from Gibco (BRL, NY). All other chemicals were purchased from Merck (Darmstadt, Germany).

(2) Preparation of K37

*Lactobacillus plantarum* subsp. *plantarum* K37 (hereinafter referred to K37) was isolated from fu-tsai, traditional fermented mustard products of Taiwan, and preserved in the stock. K37 was inoculated in MRS (de Man, Rogosa and Sharpe; pH 5.4; Difco, USA) broth, cultured at 30° C. for 21 hrs, harvested using centrifugation (1500 g, 10 min), and washed twice with sterile PBS. Then K37 was resuspended in PBS to a final concentration of $10^{10}$ CFU/ml and were stored at −20° C. until use. As for a heat-killed K37 preparation, $10^{10}$ CFU/mL of K37 were heat-killed at 100° C. for 20 min and were stored at −20° C. until use.

(3) Experimental Animals and Feeds

Four-weeks-old female BALB/c mice were purchased from the National Laboratory Animal Center, Taiwan, and maintained in National Yang-Ming University. The animal room was kept on a 12:12 hrs light-dark cycle at temperature of 25±2° C. and humidity of 55±15%. The mice were fed with a standard laboratory diet (LabDiet Autoclavable Rodent Diet 5010, PMI Nutrition International, Brentwood, USA) to acclimatize them for two weeks prior to OVA sensitization and bacterial feeding. All animal experimental procedures were reviewed and approved by the Animal Management Committee, National Yang-Ming University.

To evaluate the anti-allergic effect of K37, the 6-weeks-old mice were sensitized and challenged with OVA to establish an OVA-induced airway allergy BALB/c mice model. The experimental procedure for OVA immunization, administration of K37, and sample collection in the OVA-sensitized BALB/c mice model is summarized in FIG. 2. Five groups (n=8 in each group) of mice were assigned for a different treatment for 34 days. The healthy control group (CON) and the allergy control group (OVA) were orally administered with PBS by using stainless feeding tubes. Mice were daily fed with $10^5$ (K37-L), $10^7$ (K37-M), and $10^9$ CFU (K37-H) of heat-killed K37 as well as $10^9$ CFU of live K37 (K37-A), respectively. All groups, except for the healthy control group, were intraperitoneally injected with 100 µl of $Al(OH)_3$ containing 50 µg of OVA on day 1 and 14. The healthy control group mice received $Al(OH)_3$ only. On day 28, 29 and 30, the mice were challenged with OVA (1% in PBS, 100 µl/mouse, day) or PBS by intranasal administration. On day 32, the AHR of the mice was measured. At the endpoint of assessment, all mice were sacrificed for bronchoalveolar lavage study. The spleen was removed sterilely for further culture. The lung was removed for histological analysis.

Figure 2:
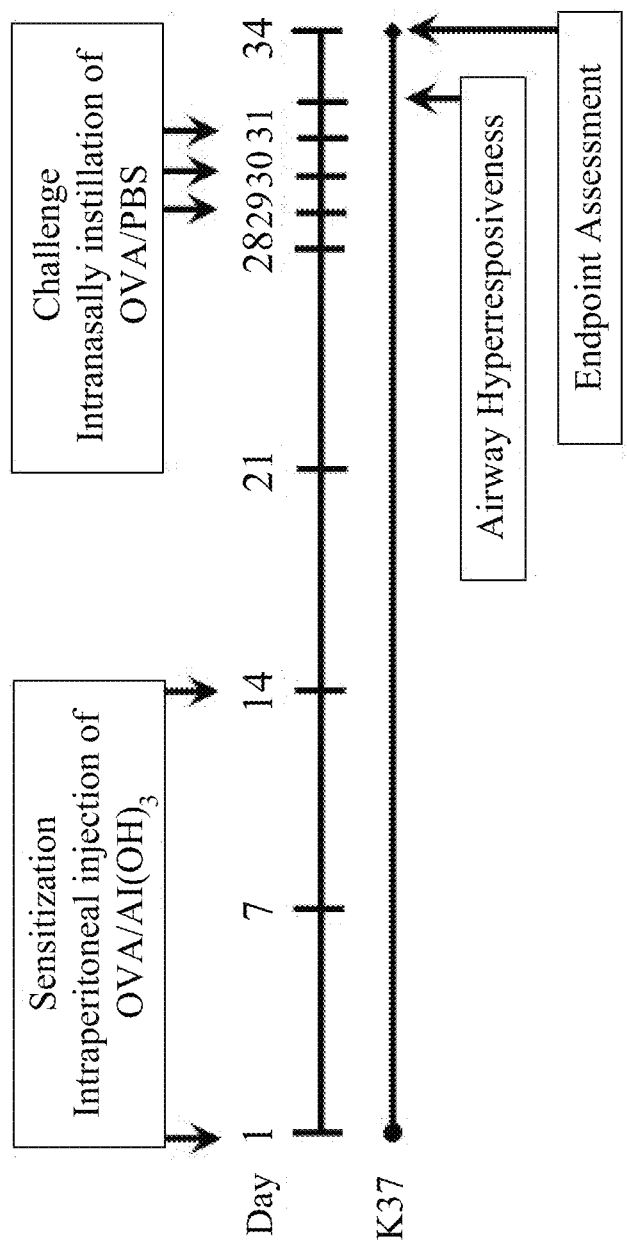
FIG. 2 shows an experimental timeline of the ovalbumin (OVA)-sensitized BALB/c mouse model. Six-weeks-old female BALB/c mice were fed with live or heat-killed *Lactobacillus plantarum* subsp. *plantarum* K37 (K37) for 4 weeks and intraperitoneally injected three times on day 1 and 14 with 50 μg of OVA in 100 μl of Al(OH)$_3$. On day 28, 29 and 30, the mice were challenged with OVA (1% in PBS, 100 μl/mouse, day) or PBS by intranasal administration. Serum was collected weekly for immunoglobulin measurement. On day 34, mice were sacrificed and spleens were removed for spleen cell preparation.

Mouse body weight was measured every day during the study period. There were no significant differences in food intake, feed efficiency, or changes in body weight among the groups. Blood was collected using retro-orbital venous plexus puncture and serum was prepared by centrifugation (2,000 rpm for 10 min) on the designated day (FIG. 2). The serum was stored at −20° C. before immunoglobulin analysis.

(4) Measurement of Airway Hyperresponsivenes (AHR)

AHR measurement was performed by whole body plethysmography. Pressure differences were measured between the main chamber of the plethysmograph containing the animal and a reference chamber (box pressure signal). Mice were challenged with aerosolized normal saline (for the baseline measurement) or methacholine (6.25, 12.5, 25, and 50 mg/mL) for three minutes and the readings were recorded and averaged for three minutes after nebulization. The enhanced pause (Penh) ratio for each minute was recorded and after the third recorded value, the average Penh value was divided by the Penh of normal saline and was presented as a relative percentage increase of Penh.

(5) Analysis of Cellular Composition of BALF

After the mice were sacrificed, the lungs were lavaged immediately via the trachea three times with 1 ml of Hanks' balanced salt solution (HBSS). The bronchoalveolar lavage fluid (BALF) was cooled on ice and centrifuged (1200 rpm, 4° C., 10 min). The supernatants were collected for the cytokine assay, and cell pellets were resuspended with 1 ml HBSS. The total numbers of cells in the BALF were counted with a standard haemocytometer. Cell counts for macrophage, eosinophil, neutrophil, and lymphocyte were performed by counting at least 200 cells in the cytocentrifuged preparations stained with Liu's stain solution (Chi I Pao, Taipei, Taiwan), and differentiated by standard morphological criteria.

(6) Preparation of Spleen Cells

Briefly, the spleen cells were adjusted to $1\times10^6$ cells/ml in RPMI 1640 culture medium supplemented with 10% FBS, 1% L-glutamate, 100 IU/ml penicillin, 0.1 mg/ml streptomycin, and 0.25 µg/ml amphotericin. The cells were cultured in a humidified incubator at 37° C. with 5% $CO_2$ for 48 hrs. After incubation, the supernatants were collected and stored at −20° C. for further cytokine analysis.

(7) Measurement of Immunoglobulins and Cytokines by Enzyme-Linked Immunosorbent Assay (ELISA)

The levels of total IgE and OVA-specific IgE, IgG1, and IgG2a were measured using the commercial ELISA kits (Bethyl Laboratory Inc., Montgomery, Tex., for total IgE and Alpha Diagnostic International Inc., San Antonio, Tex., for OVA-specific Ig). The concentrations of IL-2, IL-4, IL-5, IL-6, IL-12, IL-13, TNF-α, and IFN-γ were determined using ELISA procedure according to the manufacturers' instructions (for IL-2, IL-4, IL-10, TNF-α and IFN-γ, eBioscience, Boston, Mass.; IL-5, IL-6, IL-13, and eotaxin R&D Systems, Minneapolis, Minn.).

(8) Histological Examination of Murine Lung Tissue

After lavage, the lungs were immediately removed and fixed in 10% v/v buffered formalin (in PBS, pH 7.4) for 24 hrs, and then embedded in paraffin. The fixed and embedded tissue was then stained with hematoxylin and eosin (Sigma, St. Louis, Mo.) for histological assessment using light microscope (Leica DM750).

(9) Statistical Analysis

Data were expressed as means±standard deviation (SD). The differences between means were tested for statistical significance using a one-way ANOVA followed by a Tukey's post-hoc test. Differences between the control group and other groups were considered statistically significant when $P<0.05$ (*) or $<0.01$ (**).

2. Results

(1) Effect of Oral Administration of K37 on Immunoglobulin Expression in OVA-Sensitized Mice The levels of serum immunoglobulins were first investigated to clarify on the effects of LAB on OVA-sensitized mice. Some LAB strains with Th1-dominant responses were reported to be effective in regulating the production of OVA-induced immunoglobulins. In the present study, mice were orally administered with $10^5$ (K37-L), $10^7$ (K37-M), and $10^9$ CFU (K37-H) of heat-killed K37 as well as $10^9$ CFU of live K37 (K37-A), respectively, for 34 days and intraperitoneally injected with OVA/Al(OH)$_3$ on day 1 and 14 (FIG. 2). As shown in FIG. 3A, the total serum IgE in OVA-sensitized mice elevated after day 7 and continued to increase through day 34. The group receiving high-dose of heat-killed K37 ($10^9$ CFU, K37-H) and live K37 ($10^9$ CFU, K37-A) showed significantly reduced serum level of total IgE (FIG. 3A) and OVA-specific IgE (FIG. 3B) on day 34 compared with the OVA-sensitized group (OVA) ($P<0.01$). The serum level of OVA-specific IgG1 and the Th2-type immunoglobulin in K37-M, K37-H and K37-A groups were markedly lower than those in the OVA-sensitized group (OVA) by about 3 folds (FIG. 3C; $P<0.01$). The K37 groups had increased serum levels of OVA-specific IgG2a, the Th1-type immunoglobulin. When compared with those in the OVA-sensitized group (OVA), the levels of OVA-specific IgG2a in the K37-H and K37-A groups showed significantly different ($P<0.05$; FIG. 3D).

(2) Airway Hyperresponsiveness

Figure 4:
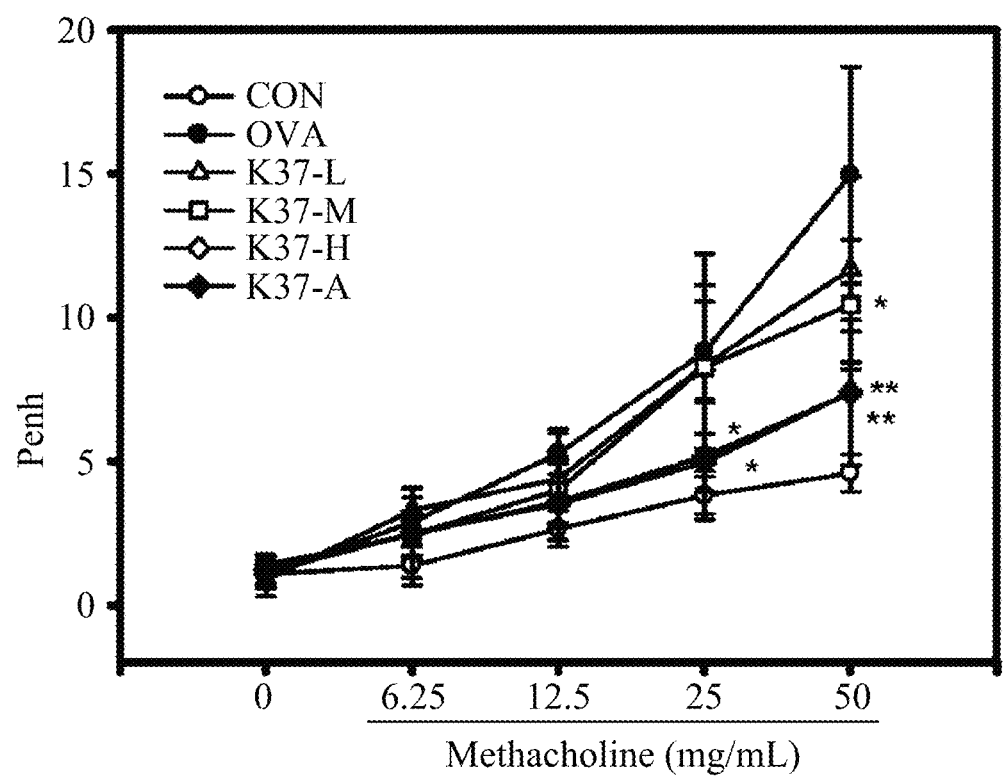
FIG. 4 shows an effect of K37 on the airway response to aerosolized methacholine measured 24 hrs after the last OVA challenge in OVA-sensitized mice as expressed by Penh. The allergy control mice (OVA group) were fed with 200 μl of PBS and sensitized and challenged with OVA. The healthy control group (CON) were fed with 200 μl of PBS and sensitized and challenged with PBS. Mice in K37 groups were fed with $10^5$ (K37-L), $10^7$ (K37-M), and $10^9$ CFU (K37-H) of heat-killed K37 as well as $10^9$ CFU of live K37 (K37-A), respectively. A difference between K37 groups and OVA group was considered statistically significant when $P<0.05$ (*) and $P<0.01$ (**).

To evaluate the effects of K37 on AHR, the assessment was performed using non-invasive whole body plethysmography 1 day after the final challenge. As shown in FIG. 4, the BALB/c mice sensitized intraperitoneally and challenged intranasally with OVA revealed an increase in the Penh value (OVA and K37 groups) in response to methacholine inhalation compared with the PBS-sensitized and PBS-challenged mice (CON group). In the OVA group, AHR to methacholine inhalation was markedly increased compared with the CON group. However, oral administration of K37 alleviated the development of AHR compared with the OVA group. The Penh levels of the K37-H and K37-A groups were similar to those of the CON group and significantly lower than those in the OVA group (methacholine 25 mg/mL, $P<0.05$; 50 mg/ml, $P<0.01$). The K37-M group showed a significantly lower Penh level at 50 mg/ml methacholine ($P<0.05$)

(3) Cell Fractionation of BALF

The cell numbers of macrophages, eosinophils, neutrophils and lymphocytes were counted to obtain the cell fractions of BALF for evaluating the effects of K37 on lung inflammation. The influx of inflammatory cells into lungs was examined. As shown in FIG. 5A, the total number of cells in BALF of the OVA group was significantly increased with AHR. The numbers of cells in K37-M, K37-H and K37-A groups were significantly lower than those in the OVA group ($P<0.05$). The cell composition of BALF was further analyzed (FIG. 5B). In the OVA group, the percentage of eosinophils and neutrophils were significantly increased while the percentage of macrophages was decreased compared with the CON group. As for the K37-H and K37-A groups, the cell number for macrophage is elevated while eosinophil infiltration is alleviated compared with the OVA group.

(4) Histologic Examination of Murine Lung Tissue

Figure 6:
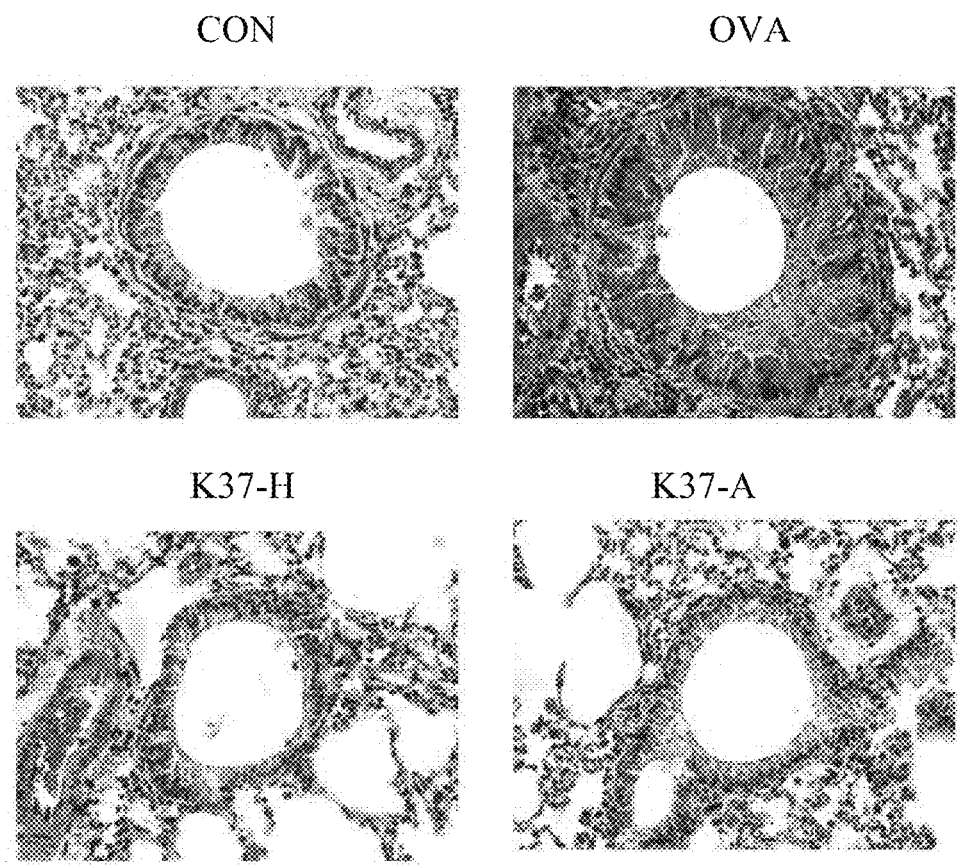
FIG. 6 shows an effect of K37 on lung tissue inflammatory cell infiltration and airway remodeling in OVA-sensitized mice after OVA challenge. Representative hematoxylin and eosin (H&E) stained section of lung tissue from the healthy control group (CON), the allergy control group (OVA), K37-H ($10^9$ CFU, heat-killed) and K37-A ($10^9$ CFU, live) groups of mice (magnification 40×).

The effect of K37 on lung inflammation in the OVA-sensitized and OVA-challenged mice was further evaluated with histological examination. As shown in FIG. 6, upon H&E staining, inflammatory changes such as increase in cell infiltration and thickness of epithelial cells were observed in OVA group. The inflammation in the peribronchial and perivascular regions of mice, which were orally administered with K37, was significantly moderate compared with that in the OVA group due to fewer cell infiltration and thinner epithelial layer (FIG. 6).

(5) Effects of Oral Administration of K37 on Cytokine Levels in BALF and Spleen Cell Culture from OVA-Sensitized Mice The cytokine production profile was employed to evaluate the effects of K37 on T-cell responses. The concentrations of Th-1 cytokines, such as IL-2, IL-12, and IFN-γ, and Th-2 cytokines, such as IL-4, IL-5, and IL-13, in BALF (FIG. 7A to 7F) and in spleen cell cultures (FIG. 8A to 8F) were measured using ELISA method. As shown in FIGS. 7A, 7C and 7E, levels of Th1 cytokines, such as IL-2, IL-12, and IFN-γ, in BALF were elevated dose-dependently in K37 groups compared with the OVA group. In the K37-H and K37-A groups, the levels of IL-2 and IL-12 were significantly higher than those in the OVA group (FIGS. 7A and 7C, $P<0.05$). The IFN-γ levels were significantly increased in K37-M ($P<0.05$), K37-H ($P<0.01$) and K37-A groups ($P<0.01$). Levels of Th2 cytokines in BALF, including IL-4, IL-5, and IL-13, were also measured. The levels of IL-4 in BALF of K37 groups (FIG. 7B) were significantly decreased compared with that in the OVA group (K37-M, $P<0.05$), K37-H and K37-A, $P<0.01$). In K37-M, K37-H and K37-A groups, the levels of IL-5 were significantly lower than that in the OVA group (FIG. 7D; K37-M, $P<0.05$, K37-H and K37-A, $P<0.01$). However, only in the K37-H and K37-A groups, the level of IL-13 was significantly diminished (FIG. 7F).

Figure 8:
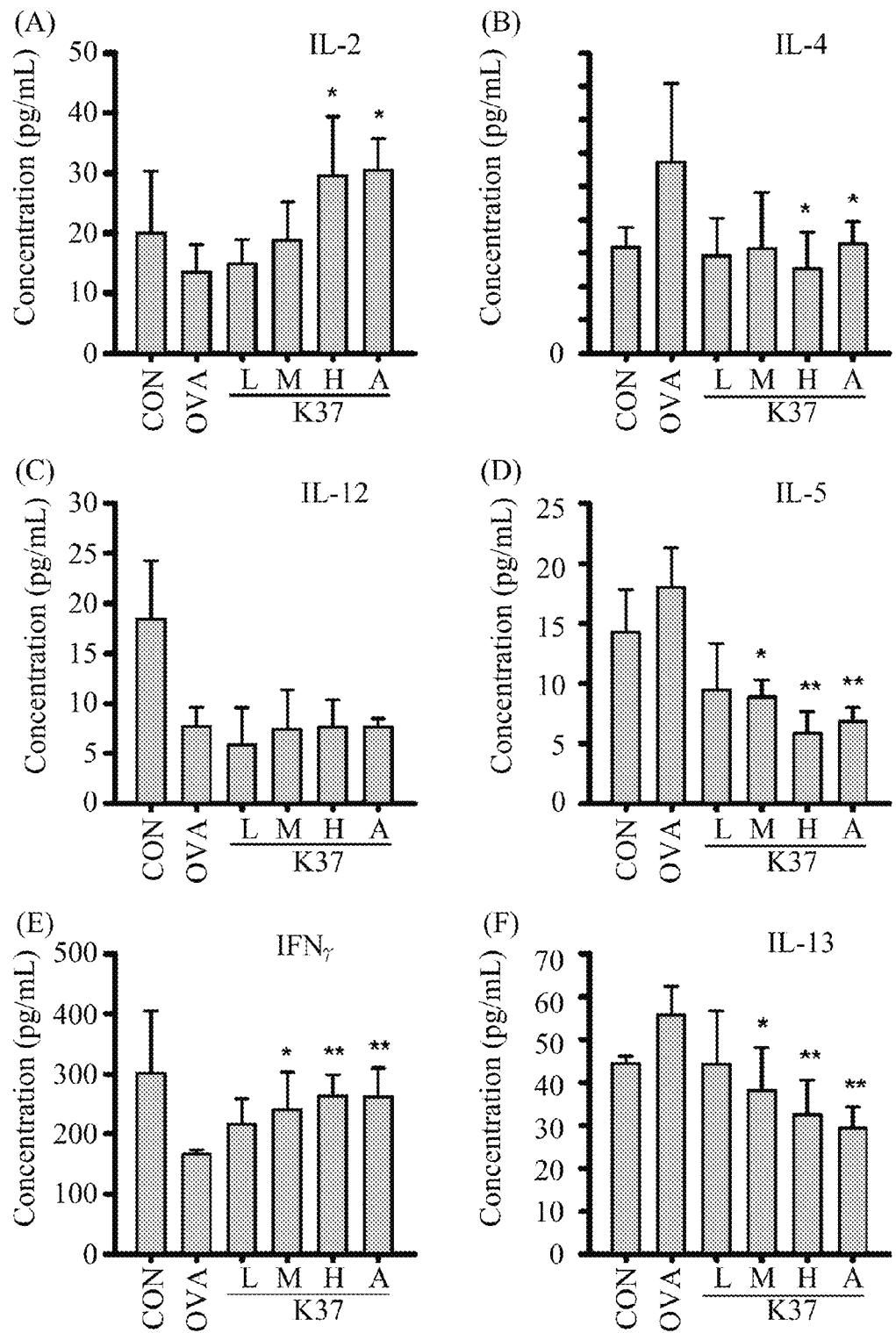
FIG. 8A to FIG. 8F show an effect of oral administration of K37 on cytokines production in spleen of OVA-sensitized mice. The concentrations of IL-2 (FIG. 8A), IL-4 (FIG. 8B), IL-12 (FIG. 8C), IL-5 (FIG. 8D), IFN-γ (FIG. 8E), and IL-13 (FIG. 8F) in the BALF were determined by ELISA. Each value represents as means±SD, n=8. A difference between K37 groups and OVA group was considered statistically significant when $P<0.05$ (*) and $P<0.01$ (**).
Figure 9:
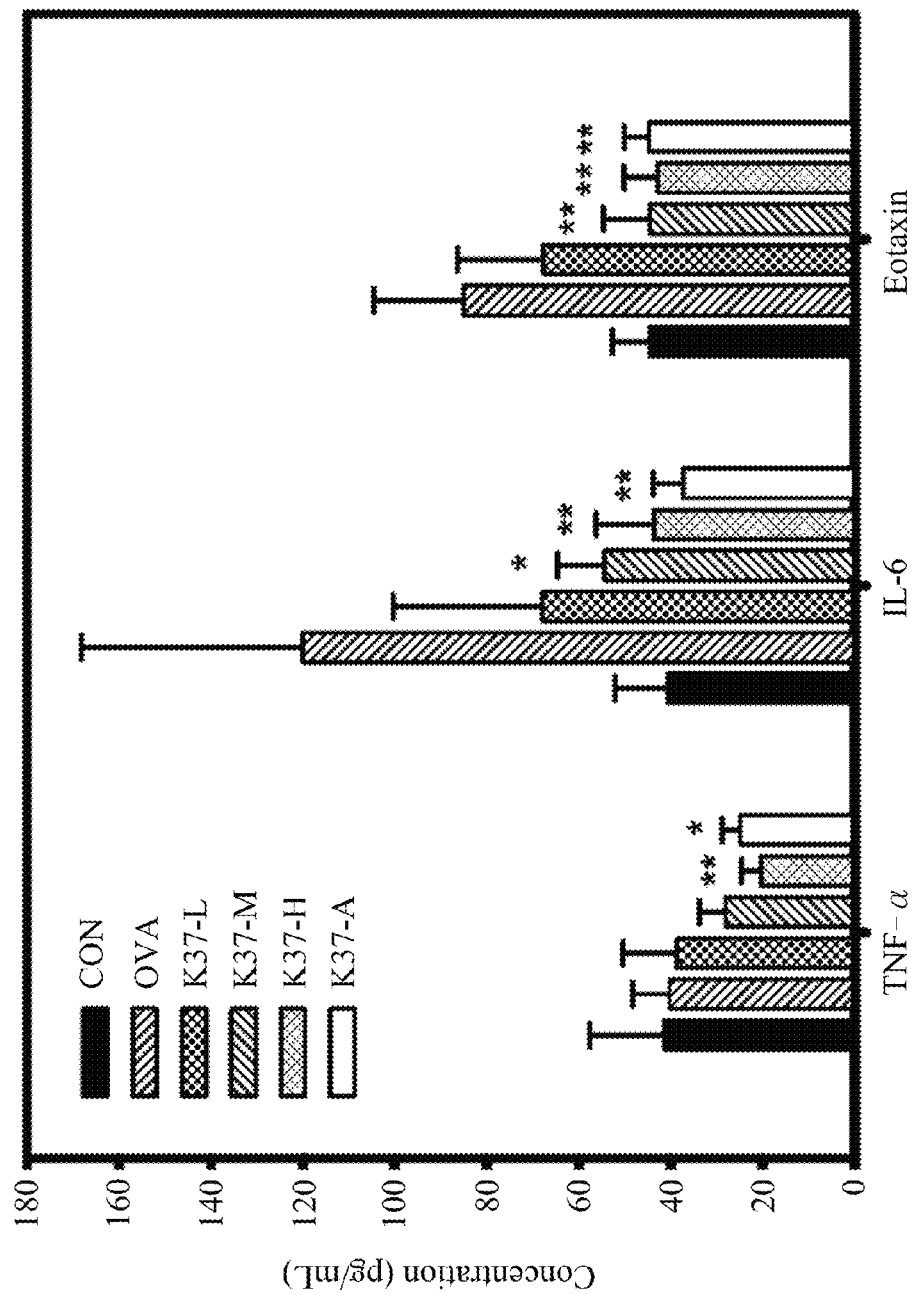
FIG. 9 shows an effect of oral administration of *Lactobacillus plantarum* subsp. *plantarum* K37 (K37) on levels of pro-inflammatory cytokines, such as TNF-α, IL-6, and eotaxin, in BALF. A difference between K37 groups and OVA group was considered statistically significant when $P<0.01$ (**).

As for the cytokines in spleen cells, the levels of IL-2 (FIG. 8A) in K37 groups were elevated compared with that in the OVA group; however, only the increases in the K37-H and K37-A groups showed statistical significance ($P<0.05$). In all OVA-sensitized groups (OVA and K37 groups), the levels of IL-12 were comparable and lower than that in the non-sensitized group (CON group) (FIG. 8C). In K37-M, K37-H, and K37-A groups, the levels of IFN-γ were higher than that in the OVA group, showing statistical significance ($P<0.05$ and $P<0.01$, respectively). The reduced IL-4 levels were observed in K37 groups (K37-H and K37-A $P<0.05$). The levels of IL-5 and IL-13 were elevated dose-dependently in K37 groups ($P<0.05$ for K37-M and $P<0.01$ for K37-H and K37-A). However, the levels of IL-4 were comparable in all groups (FIG. 8B). Taken together, the results of cytokine determination suggested that K37 treatment induced the production of Th-1 cytokines, IL-2 and IFN-γ, in BALF and spleen cell culture. Diminished secretion of Th2 cytokines, IL-4, IL-5 and IL-13, was observed in K37 groups. The levels of proinflammatory cytokines, such as TNF-α and IL-6, and eotaxin, in BALF were also measured to evaluate the effects of K37 on inflammation status in lung. As shown in FIG. 9, the levels of TNF-α were comparable in CON and OVA groups but dose-dependently decreased in K37 groups. The levels of IL-6 and eotaxin were dramatically elevated in the OVA group compared with the CON group. However, the levels of IL-6 and eotaxin in K37-H and K37-A groups were comparable to those in the CON groups. The levels of TNF-α and IL-6 in spleen cell culture showed the same tendency as in BALF (data not shown). Taken together, K37 treatment decreased the production of TNF-α, IL-6 and eotaxin in BALF of OVA-sensitized mice.

The present invention investigates the effects of orally administered K37 on OVA-induced allergic asthma in BALB/c mice model. The present results shows that K37 suppresses allergic parameters, including AHR, airway inflammation, total IgE and OVA-specific IgE. The cytokine production profiles in BALF and spleen cell culture reveal that K37 skews immune responses toward Th-1 responses, elevates levels of Th-1 cytokines, and diminish levels of Th-2 cytokines. The levels of inflammatory mediators in BALF, such as TNF-α, IL-6 and eotaxins, are dose-dependently decreased by K37 oral administration. The lower cell numbers of eosinophils and neutrophils in BALF suggest that inflammation is ameliorated by K37. The histological observation on lung sections also shows infiltration of fewer cells.

K37 isolated from fu-tsai, traditional fermented mustard products of Taiwan, was previously evaluated for the effect on in vitro production of cytokines by hPBMCs. Consequently, it is speculated that lactic acid bacteria with an in vitro Th1-polarizing potential might exhibit anti-allergic effects in vivo.

Figure 3:
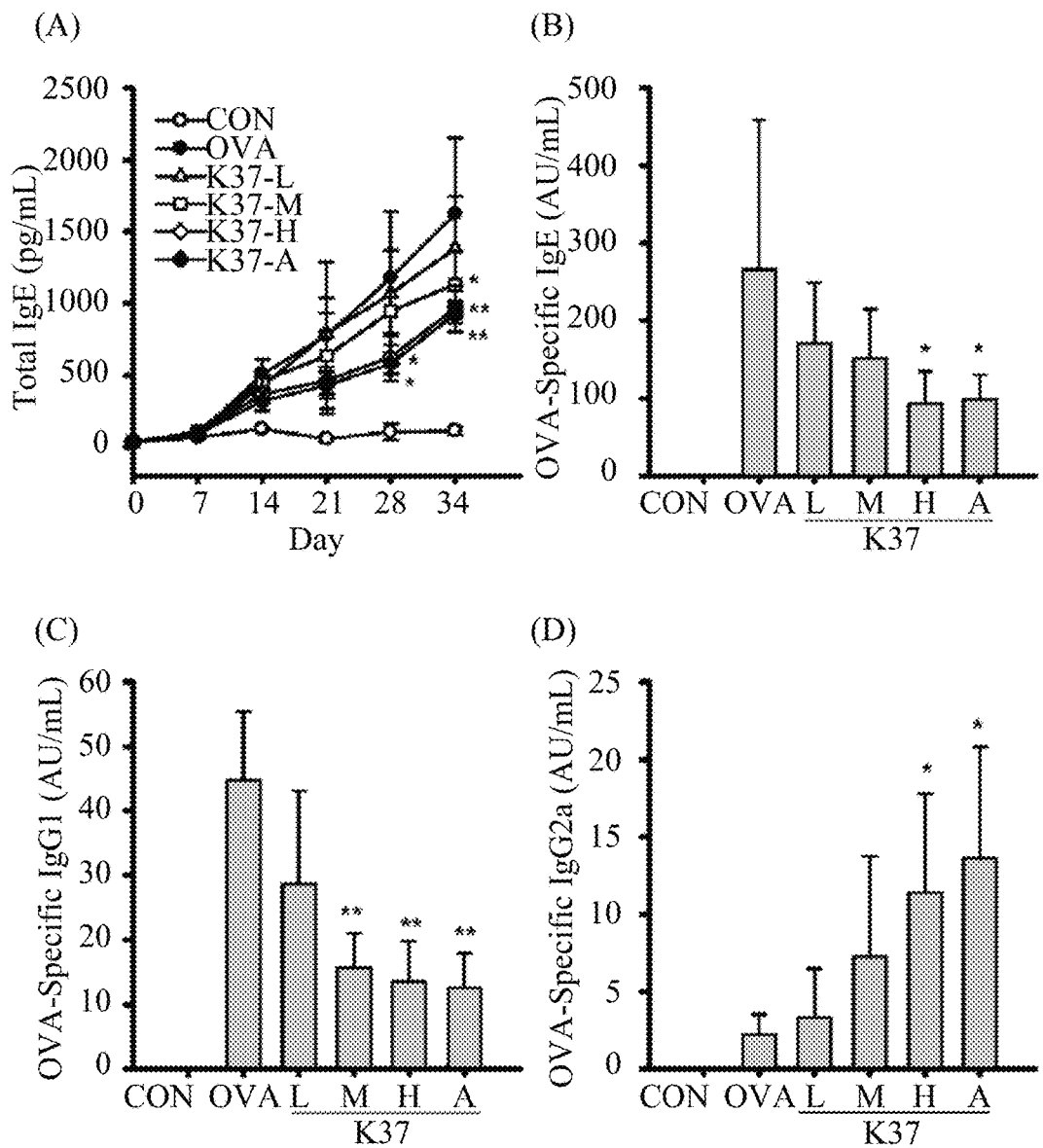
FIG. 3A to FIG. 3D show an effect of oral administration of K37 on immunoglobulin production in OVA-sensitized mouse serum. BALB/c mice were fed with $10^5$ (K37-L), $10^7$ (K37-M), and $10^9$ CFU (K37-H) of heat-killed K37 as well as $10^9$ CFU of live K37 (K37-A), respectively, from day 1 to day 34, and intraperitoneally injected on day 1 and 7 with 50 μg OVA in 100 μl $Al(OH)_3$. Both of the healthy control group (CON) and the allergy control group (OVA) were administered with PBS orally during the experimental period, and the CON group was not OVA-sensitized. Serum levels of total IgE (FIG. 3A), OVA-specific IgE (FIG. 3B), OVA-specific IgG1 (FIG. 3C), and OVA-specific IgG2a (FIG. 3D) were determined by ELISA. Each value represents means±SD, (n=8). A difference between K37 groups and OVA group was considered statistically significant when $P<0.05$ (*) and $P<0.01$ (**).

Ovalbumin (OVA) is the most frequently used allergen in animal models of allergy. The lower the levels of IgE and OVA-specific IgE and IgG1, the more moderate the allergic responses are. In the present invention, the intraperitoneally OVA-sensitized and intranasally OVA-challenged BALB/c model (FIG. 2) was employed to investigate the anti-allergic effects of K37. As shown in FIG. 3, the increased levels of serum IgE, OVA-specific IgE, and IgG1 in the OVA group indicates the allergic animal model is established and represents B-cell type Th-2 responses. In K37 groups, the levels of total IgE, OVA-specific IgE, and OVA-specific IgG1 are significantly lower than the OVA group at the endpoint of assessment (K37-M, P<0.05; and K37-A P<0.01) (FIG. 3). Furthermore, considerable increase of OVA-specific IgG2a was observed in the K37 group (FIG. 3D). The results of serum immunoglobulin analysis demonstrate systemic anti-allergic effects of K37. Moreover, the modulatory effects of K37 on OVA-induced immunoglobulins secretion show a dose-dependent tendency.

The present results reveals that K37 exhibits both of systemic and airway anti-allergic effects and K37-H ($10^9$ CFU, heat-killed) and K37-A ($10^9$ CFU, live) show the best activity, suggests that the anti-allergic effects of K37 are dose-dependent.

Hyperresponsiveness is defined as increased sensitivity to some cholinergic agents, like methacholine, which leads to smooth muscle constrictions and increases airway resistance by narrowing the airways. Asthma is one of the airway hyperresponsive diseases which can be characterized by the accumulation of inflammatory cells, increase in mucus production, release of certain Th2 cytokines, IL-4, IL-5, and IL-13, and increased levels of IgE. In the present invention, the changes in airway remodeling of K37 treatment were investigated. K37 markedly alleviates the OVA-induced AHR to inhaled methacholine (FIG. 4). According to lung histopathological studies with H&E staining, inflammatory cell infiltration is inhibited in the K37 groups compared with the OVA group (FIG. 6).

Figure 7:
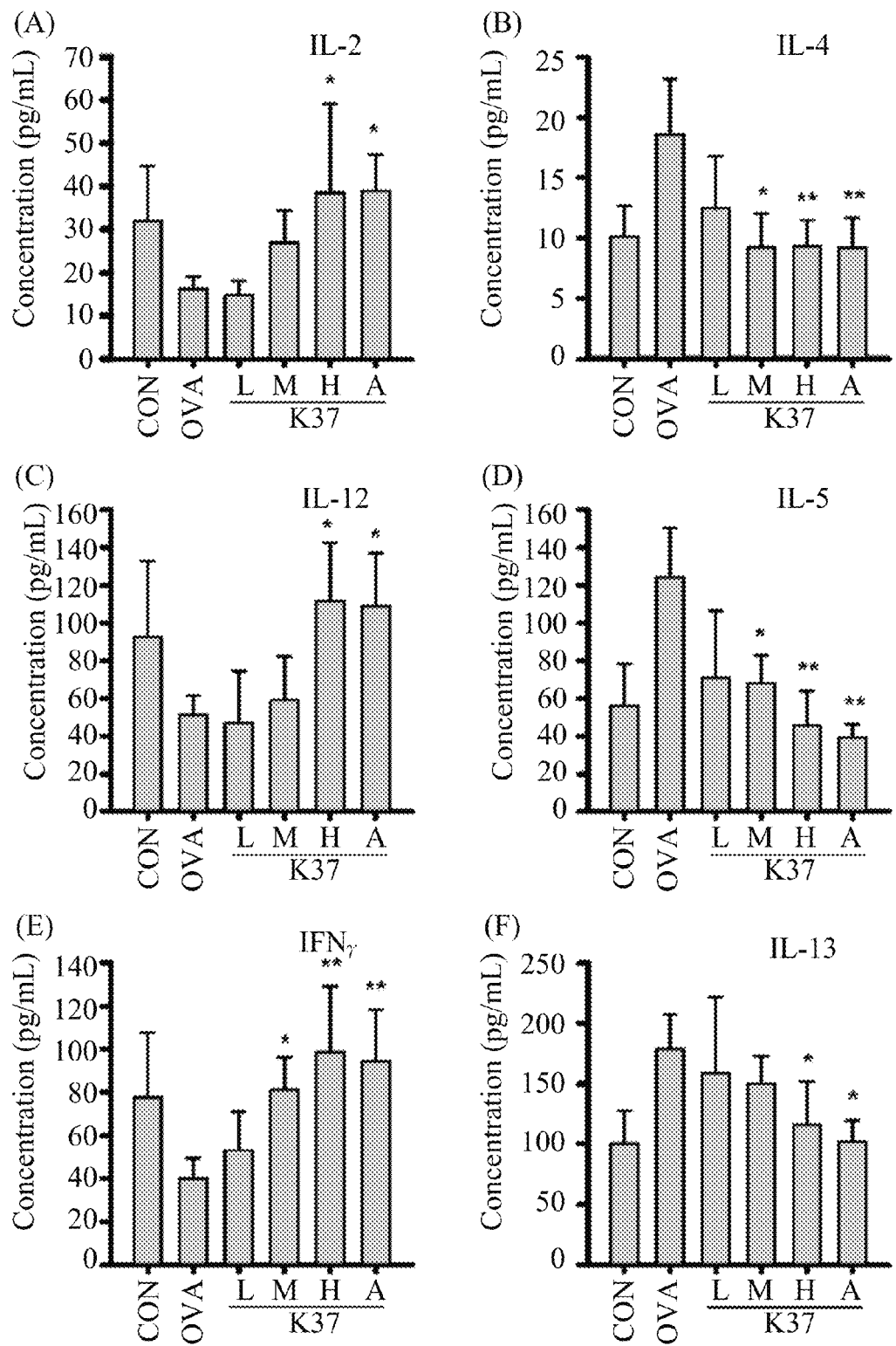
FIG. 7A to FIG. 7F show an effect of oral administration of K37 on cytokine production in BALF of OVA-sensitized mice. The concentration of IL-2 (FIG. 7A), IL-4 (FIG. 7B), IL-12 (FIG. 7C), IL-5 (FIG. 7D), IFN-γ (FIG. 7E), and IL-13 (FIG. 7F) in the BALF were determined by ELISA. Each value represents as means±SD, n=8. A difference between K37 groups and OVA group was considered statistically significant when $P<0.05$ (*) and $P<0.01$ (**).

Cytokine expressions, such as IL-4, IL-5, and IL-13, in connection with T-cell response, and immunoglobulin G1 (IgG1) production in connection with B-cell response, are thought to be related to Th2 immunity. Th2 cytokines play an important role in asthma. Among Th2 cytokines, IL-4 drives naïve T helper cells to be the Th2 phenotype and induces B cells to switch the isotype to IgE. IL-5 produced by Th2 cells is responsible for eosinophil growth, differentiation, mobilization, recruitment, activation and survival. IL-13 plays a critical role in the pathogenesis of asthma. Excessive productions of IL-4, IL-5, and IL-13 are implicated in the development of asthma. The present results shows increased T-cell responsive Th2 cytokines, such as IL-4, IL-5 and IL-13, in both of BALF and cultured spleen cells from OVA groups (FIG. 6 and FIG. 7, respectively). Evidences have shown that Th1/Th2 regulatory effects of LAB are useful in allergic animal model. In the present invention, AHR is decreased by oral administration of K37, and suggests its anti-allergic effects which may be attributed to the reduction of Th-2 cytokines and eotaxin is well known to play an important role in the development of AHR. It is speculated that the inhibitory effects on IL-13 contributed to the anti-allergic activity of K37 (FIGS. 7F and 8F). Besides inhibition on Th-2 cytokines, K37 also enhances production of Th-1 cytokines. K37 elevates IFN-γ production in hPB-MCs (data not shown). K37 also increases the levels of IL-2, IL-12 and IFN-γ in BALF and spleen cell culture (FIGS. 7 and 8, respectively). Taken together, the present results indicate that K37 has a promising effect on modulating T-cell responses in OVA-sensitized mice toward Th1 responses.

Figure 5:
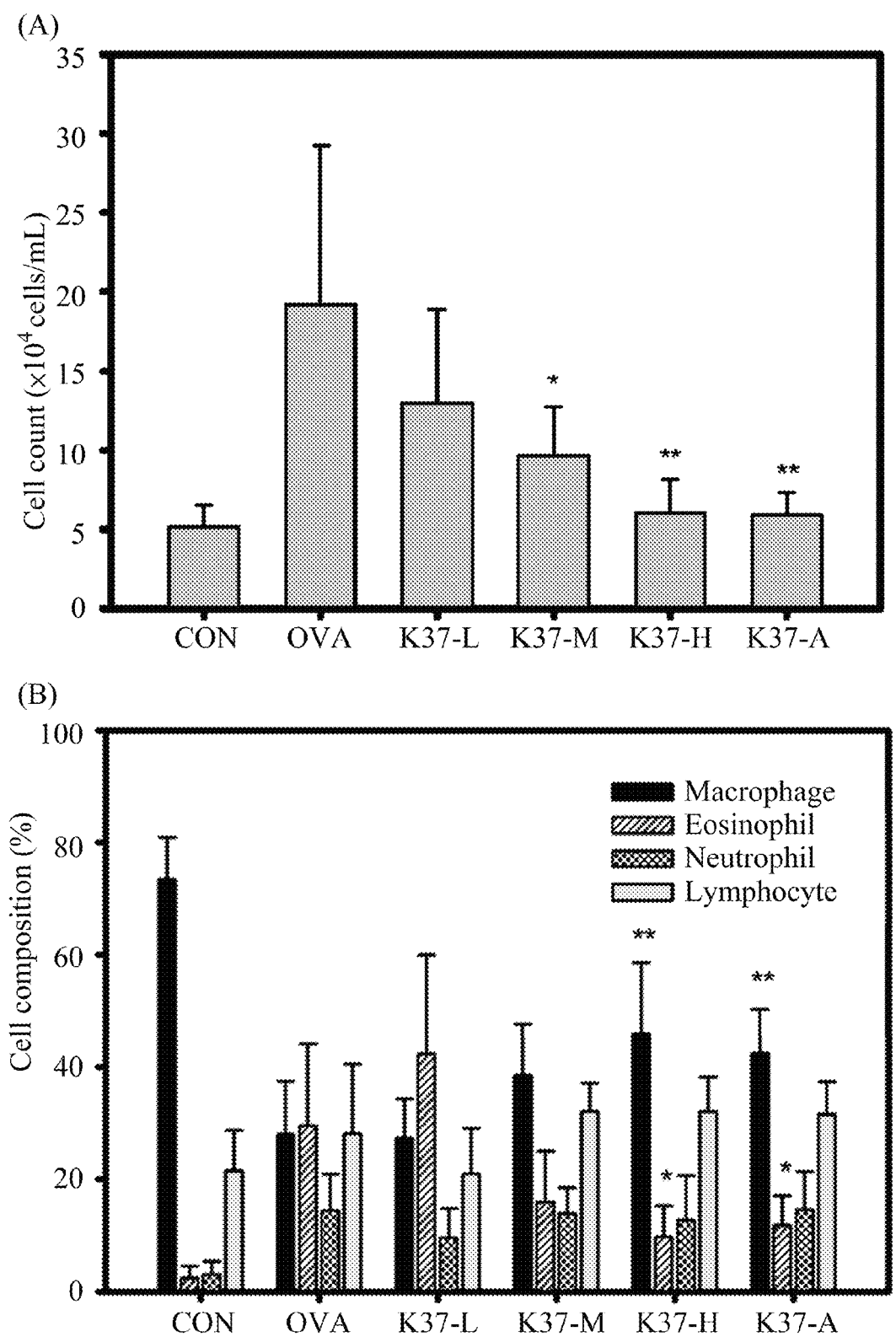
FIG. 5A and FIG. 5B show an effect of K37 on lung tissue inflammatory cell infiltration in OVA-sensitized mice after OVA challenge.

Inflammation in lung tissue and BALF induces by OVA sensitization and challenge was observed in the present invention (FIGS. 5 and 6). Many types of inflammatory cells are involved in the process of airway inflammation, such as mast cells, eosinophils, and T lymphocytes. Among those cells, eosinophils play the crucial role in the pathogenesis of allergic diseases. Eosinophils are attracted via CC chemokine receptor 3 (CCR3) to chemoattractants, such as eotaxin released in the airway. Clinical and experimental studies have established eosinophilia as a sign of allergic disorders. K37 lowers the levels of OVA-specific IgE as well as total IgE. Furthermore, OVA-specific IgG1 is decreased in K37 groups (FIG. 3).

Eotaxin is regarded as an important aspect of allergy because it induces the recruitment of eosinophils, basophils, and Th2 lymphocytes in lungs. The peribronchial and perivascular inflammatory infiltrate generally consisted of eosinophils and mast cells. As shown in FIG. 5B, the number of eosinophils is significantly decreased in the K37-H and K37-A groups compared with the OVA group. Moreover, the infiltration of eosinophils was observed in the peribronchial regions of the lung section of the OVA group. However, fewer cells infiltrated in the K37 groups (FIG. 6). Furthermore, the levels of eotaxin in K37-M, K37-H and K37-A groups are comparable to that in the CON group. Decrease of TNF-α and IL-6 in the K37-H group and K37-A group were also observed (FIG. 9). Taken together, these results suggest that moderate inflammation in lung contributed to the anti-allergic effects of K37.

In summary, the present invention demonstrates that K37 could ameliorate asthma-like responses in OVA-sensitized BALB/c mice. In the evaluation of AHR by means of enhanced pause (Penh) with whole body plethysmography, it is found that the administration of K37 could significantly decrease AHR in OVA-immunized BALB/c mice. K37 induces pronounced immunomodulatory effects on most of the parameters tested. Thus, K37 can be a promising candidate for protection and prophylactic treatment of allergic diseases.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claim.

What is claimed is:

1. An isolated lactic acid bacterium for immunomodulation, being *Lactobacillus plantarum* subsp. *plantarum* K37 strain deposited in DSME-DEUTSCHE SAMMLUNG VON MIKROORGANISMEN UND ZELLKULTUREN GmbH under Accession No. DSM 27445, wherein the lactic acid bacterium is a heat-inactivated bacterium being heat-inactivated at 100° C. for 20 min.

2. A pharmaceutical composition for immunomodulation in a subject, comprising:
   the lactic acid bacterium of claim 1; and
   an excipient.

3. The pharmaceutical composition of claim 2, wherein the pharmaceutical composition is orally administered to the subject.

4. The pharmaceutical composition of claim 2, wherein an amount of at least one selected from the group consisting of macrophage, eosinophil, neutrophil and lymphocyte is decreased in the subject.

5. The pharmaceutical composition of claim 2, wherein the immunomodulation is related to an expression of a protein selected from the group consisting of IgG1, IgG2a, IgE, INF-γ, TNF-α, IL-2, IL-4, IL-5, IL-6, IL-13 and eotaxin.

6. The pharmaceutical composition of claim 5, wherein the expression of IL-2, IL-12 and IFN-γ is increased.

7. The pharmaceutical composition of claim 5, wherein the expression of IL-4, IL-5, IL-13, TNF-α, eotaxin and IgE is decreased.

8. A method for modulating the immune system in a subject, comprising a step of administering an effective amount of the lactic acid bacterium of claim 1 to the subject.

9. The method of claim 8, wherein the lactic acid bacterium is orally-administered to the subject.

10. The method of claim 8, wherein an amount of at least one selected from the group consisting of macrophage, eosinophil, neutrophil and lymphocyte is decreased in the subject.

11. The method of claim 8, wherein an expression of a protein selected from the group consisting of IgG1, IgG2a, IgE, IFN-γ, TNF-α, IL-2, IL-4, IL-5, IL-6, IL-12, IL-13 and eotaxin is modulated.

12. The method of claim 11, wherein the expression of IL-2, IL-12 and INF-γ is increased.

13. The method of claim 11, wherein the expression of IL-4, IL-5, IL-13, TNF-α, eotaxin and IgE is decreased.

* * * * *